US012330667B2

(12) United States Patent
Kaldobsky et al.

(10) Patent No.: US 12,330,667 B2
(45) Date of Patent: Jun. 17, 2025

(54) WAKE-UP SEQUENCE CALIBRATION

(71) Applicant: Ford Global Technologies, LLC, Dearborn, MI (US)

(72) Inventors: Tyler James-Ray Kaldobsky, Canton, MI (US); Brendan Jenkins, Canton, MI (US); Daniel Sullivan, West Bloomfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 269 days.

(21) Appl. No.: 18/189,241

(22) Filed: Mar. 24, 2023

(65) Prior Publication Data

US 2024/0317247 A1 Sep. 26, 2024

(51) Int. Cl.
*G08B 21/06* (2006.01)
*A61B 5/00* (2006.01)
*B60K 28/06* (2006.01)
*B60W 50/06* (2006.01)
*B60W 50/10* (2012.01)
*B60W 50/16* (2020.01)

(52) U.S. Cl.
CPC .......... *B60W 50/06* (2013.01); *A61B 5/4806* (2013.01); *B60K 28/06* (2013.01); *B60W 50/10* (2013.01); *B60W 50/16* (2013.01); *G08B 21/06* (2013.01); *B60W 2420/403* (2013.01); *B60W 2540/043* (2020.02); *B60W 2540/22* (2013.01); *B60W 2540/221* (2020.02); *B60W 2756/00* (2020.02)

(58) Field of Classification Search
CPC ...... G08B 21/06; G08B 21/0407; A61B 5/18; A61B 5/4806; B60K 28/06
See application file for complete search history.

(56) References Cited

U.S. PATENT DOCUMENTS

| 6,218,947 | B1 | 4/2001 | Sutherland | |
| 6,888,779 | B2 * | 5/2005 | Mollicone | H05B 47/12 |
| | | | | 368/10 |
| 7,427,924 | B2 | 9/2008 | Ferrone et al. | |
| 8,493,220 | B2 | 7/2013 | Virtanen et al. | |
| 8,521,439 | B2 * | 8/2013 | Mott | G16H 40/63 |
| | | | | 702/19 |
| 8,725,311 | B1 | 5/2014 | Breed | |
| 8,948,861 | B2 | 2/2015 | Rai et al. | |
| 9,129,505 | B2 | 9/2015 | Breed et al. | |
| 9,129,508 | B2 | 9/2015 | Kuntzel | |
| 9,466,200 | B2 * | 10/2016 | Berezhnyy | G08B 21/18 |
| 9,725,036 | B1 * | 8/2017 | Tarte | B60W 50/16 |

(Continued)

*Primary Examiner* — John A Tweel, Jr.
(74) *Attorney, Agent, or Firm* — Frank A. MacKenzie; Brooks Kushman P.C.

(57) ABSTRACT

A system and a method for calibrating a wake-up sequence for a user includes determining that the user is asleep based upon sensor data, activating one or more stimulus mechanisms for a set period of time in a test wake-up sequence upon occurrence of a wake-up condition, determining an elapsed time within the set period of time of the one or more stimulus mechanisms being activated in the test wake-up sequence at which the user wakes from sleep based on additional sensor data, comparing the elapsed time to a threshold time indicative of a sufficient wake-up time, and determining a calibrated wake-up sequence including the one or more stimulus mechanisms having elapsed times below the threshold time.

20 Claims, 2 Drawing Sheets

(56) References Cited

U.S. PATENT DOCUMENTS

| | | | |
|---|---|---|---|
| 10,362,980 B2 | 7/2019 | Kusukame et al. | |
| 10,783,587 B1 | 9/2020 | Augustine et al. | |
| 11,180,158 B1 | 11/2021 | Lyle | |
| 11,594,111 B2* | 2/2023 | Read | A61B 5/01 |
| 2012/0154156 A1 | 6/2012 | Kuntzel | |
| 2013/0208576 A1* | 8/2013 | Loree, IV | G04G 11/00 |
| | | | 368/256 |
| 2024/0399085 A1* | 12/2024 | Shouldice | G16H 50/20 |

* cited by examiner

WAKE-UP SEQUENCE CALIBRATION

BACKGROUND

Various environments may accommodate sleeping persons. An individual may be attempted to be awoken in a timely manner with a wake-up stimulus in various situations. However, different individuals may respond to a wake-up stimulus differently.

DETAILED DESCRIPTION

Figure 1:
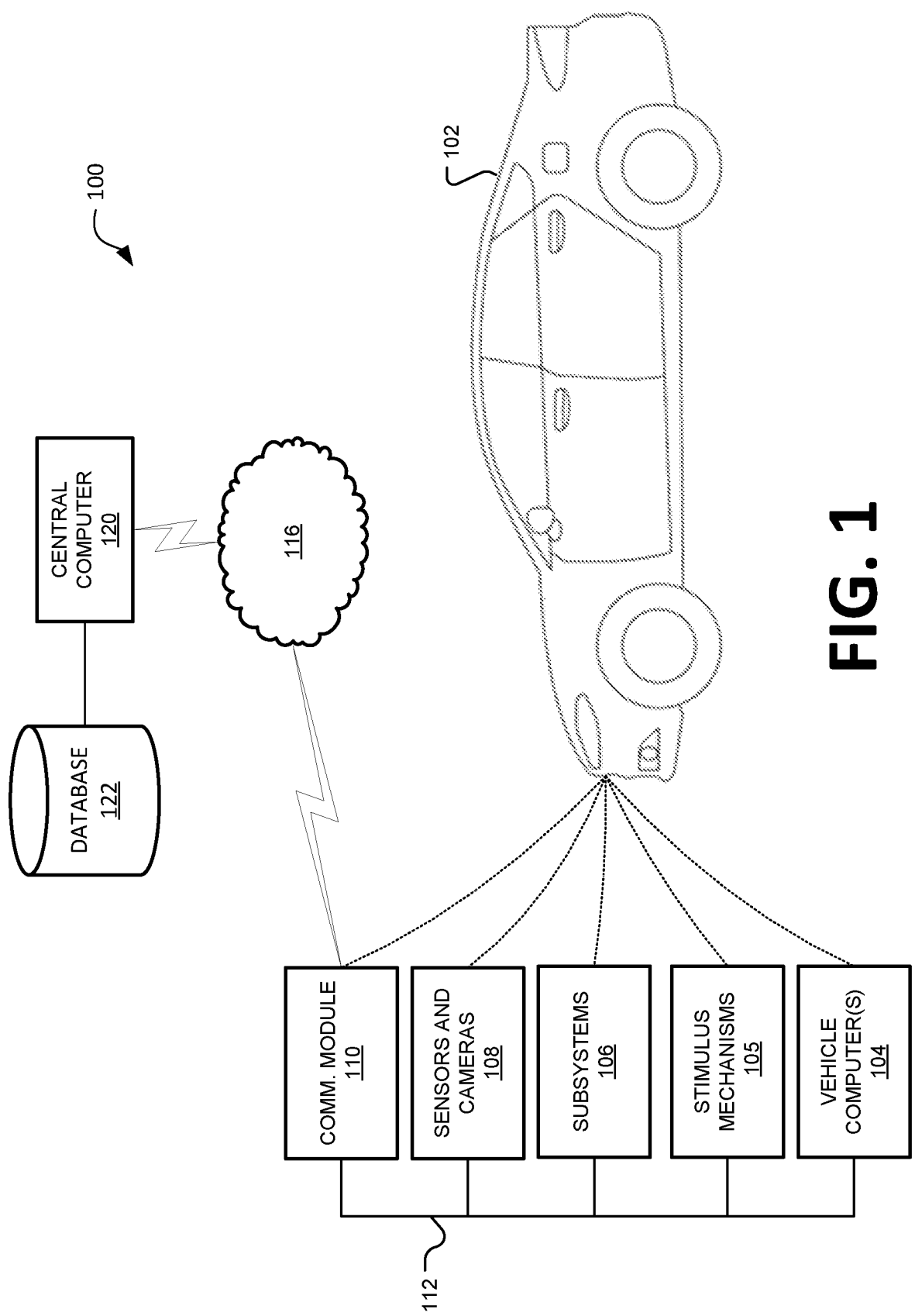
FIG. 1 is diagram of an example system for calibration of a wake-up sequence.

The present disclosure describes a system and method for calibrating a wake-up sequence for a user with a test wake-up sequence in order to learn effective stimulus for waking the user.

A calibrated wake-up sequence for a user may be determined empirically based upon exposure to various test wake-up sequences. Upon determining that the user is asleep based upon sensor data, one or more stimulus mechanisms of a test wake-up sequence may be activated for a set period of time upon occurrence of a wake-up condition. When a stimulus mechanism wakes the user from sleep, an elapsed time of the particular stimulus mechanism being activated in the test wake-up sequence can be recorded. The elapsed time can be compared to a threshold time indicative of a sufficient wake-up time in order to identify stimulus mechanisms that are effective for the user. A calibrated wake-up sequence for the user can then be created that includes the stimulus mechanisms having elapsed times below the threshold time.

In one or more implementations, a system may include a computer including a processor and a memory. The memory stores instructions executable by the processor programmed to: determine that a user is asleep based upon sensor data; activate one or more stimulus mechanisms for a set period of time in a test wake-up sequence upon occurrence of a wake-up condition; determine an elapsed time within the set period of time of the one or more stimulus mechanisms being activated in the test wake-up sequence at which the user wakes from sleep based on additional sensor data; compare the elapsed time to a threshold time indicative of a sufficient wake-up time; and determine a calibrated wake-up sequence including the one or more stimulus mechanisms having elapsed times below the threshold time.

In an implementation, the system may further include instructions executable by the processor programmed to: initiate the system upon an activation by the user; prompt the user for continued use of the system upon determining the calibrated wake-up sequence; and terminate the system upon a deactivation by the user.

In another implementation, the system may further include instructions executable by the processor programmed to: determine an identity of the user; order, within the calibrated wake-up sequence, the one or more stimulus mechanisms having elapsed times below the threshold time based upon lower elapsed times; and store the calibrated wake-up sequence for the user based upon the identity.

In a further implementation, the one or more stimulus mechanisms include a light source, a sound transducer, a haptic/vibration transducer, and/or a climate control system.

In an implementation, the test wake-up sequence may include an ordered sequence of the one or more stimulus mechanisms including activation of a first stimulus mechanism, activation of a second stimulus mechanism, activation of a third stimulus mechanism, activation of a fourth stimulus mechanism, and activations of various combinations of the first, second, third, and fourth stimulus mechanisms; and the activation of the first, second, third, and/or fourth stimulus mechanisms may increase in intensity over an activation time.

In another implementation, the sensor data and the additional sensor data may be from a user-monitoring camera, a motion sensor, a heart-rate sensor, a respiration sensor, a stress sensor, a touch sensor, and/or a force sensor.

In a further implementation, the system may further include instructions executable by the processor programmed to vary the stimulus mechanisms or an or order of the stimulus mechanisms in the test wake-up sequence to refine the calibrated wake-up sequence.

In an implementation, the system may further include instructions executable by the processor programmed to transmit the calibrated wake-up sequence for the user to a remote server.

In another implementation, the system may further include comprising instructions executable by the processor programmed to receive a default wake-up sequence from the remote server based upon aggregated wake-up sequences of a plurality of users.

In a further implementation, the computer may be a vehicle computer, wherein the sensor data and the additional sensor data may be provided by sensors in a vehicle, and wherein the one or more stimulus mechanisms may be disposed in the vehicle.

In one or more implementations, a method may include: determining that a user is asleep based upon sensor data; activating one or more stimulus mechanisms for a set period of time in a test wake-up sequence upon occurrence of a wake-up condition; determining an elapsed time within the set period of time of the one or more stimulus mechanisms being activated in the test wake-up sequence at which the user wakes from sleep based on additional sensor data; comparing the elapsed time to a threshold time indicative of a sufficient wake-up time; and determining a calibrated wake-up sequence including the one or more stimulus mechanisms having elapsed times below the threshold time.

In an implementation, the method may further include: initiating the method upon an activation by the user; prompting the user for continued use of the method upon determining the calibrated wake-up sequence; and terminating the method upon a deactivation by the user.

In another implementation, the method may further include: determining an identity of the user; ordering, within the calibrated wake-up sequence, the one or more stimulus mechanisms having elapsed times below the threshold time based upon lower elapsed times; and storing the calibrated wake-up sequence for the user based upon the identity.

In an implementation, the one or more stimulus mechanisms may include a light source, a sound transducer, a haptic/vibration transducer, and/or a climate control system.

In another implementation, the test wake-up sequence may include an ordered sequence of the one or more stimulus mechanisms including activation of a first stimulus mechanism, activation of a second stimulus mechanism, activation of a third stimulus mechanism, activation of a fourth stimulus mechanism, and activations of various combinations of the first, second, third, and fourth stimulus mechanisms, and the activation of the first, second, third, and/or fourth stimulus mechanisms may increase in intensity over an activation time.

In a further implementation, the sensor data and the additional sensor data may be from a user-monitoring camera, a motion sensor, a heart-rate sensor, a respiration sensor, a stress sensor, a touch sensor, and/or a force sensor.

In an implementation, the method may further include varying the stimulus mechanisms or an order of the stimulus mechanisms in the test wake-up sequence to refine the calibrated wake-up sequence.

In another implementation, the method may further include transmitting the calibrated wake-up sequence for the user to a remote server.

In a further implementation, the method may further include receiving a default wake-up sequence from the remote server based upon aggregated wake-up sequences of a plurality of users.

In an implementation, the user may be in a vehicle, wherein the sensor data and the additional sensor data may be provided by sensors in the vehicle, and wherein the one or more stimulus mechanisms may be disposed in the vehicle.

With reference to FIG. 1, an example environment where a user may need to be woken may include parked vehicle 102 in a connected vehicle system 100 that can provide communications between a vehicle 102 and a central computer 120 to share data. Although the following example describes the present disclosure with respect to a ground vehicle 102, this is merely one example. Other example environments where a user may need to be woken include, but are not limited to, transportation environments including other stopped or parked vehicles such as aircraft, trains, and boats, work environments such as kiosks and other workstations, and home environments such as bedrooms and home theaters.

With continued reference to FIG. 1, the vehicle 102 may be any type of passenger or commercial automobile such as a car, a truck, a sport utility vehicle, a crossover, a van, a minivan, a taxi, a bus, etc. The vehicle 102, for example, may be an autonomous vehicle. In other words, the vehicle 102 may be autonomously operated such that the vehicle 102 may be driven without constant attention from a driver, i.e., the vehicle 102 may be self-driving without human input.

Vehicle 102 is a set of components or parts, including hardware components and typically also software and/or programming, to perform a function or set of operations in the vehicle 102. Vehicle subsystems 106 typically include a braking system, a propulsion system, and a steering system as well as other subsystems including but not limited to an advanced driver assist system (ADAS), a body control system, a climate control system, a lighting system, and a human-machine interface (HMI) system, which may include a heads-up display (HUD), an instrument panel, and infotainment system. The propulsion subsystem converts energy to rotation of vehicle 102 wheels to propel the vehicle 102 forward and/or backward. The braking subsystem can slow and/or stop vehicle 102 movement. The steering subsystem can control a yaw, e.g., turning left and right, maintaining a straight path, of the vehicle 102 as it moves.

Computers, including the herein-discussed one or more vehicle computers 104, (e.g., one or more electronic control units (ECUs), and central computer 120 include respective processors and memories. A computer memory can include one or more forms of computer readable media, and stores instructions executable by a processor for performing various operations, including as disclosed herein. For example, the computer can be a generic computer with a processor and memory as described above and/or an ECU, controller, or the like for a specific function or set of functions, and/or a dedicated electronic circuit including an ASIC that is manufactured for a particular operation, e.g., an ASIC for processing sensor data and/or communicating the sensor data. In another example, computer may include an FPGA (Field-Programmable Gate Array) which is an integrated circuit manufactured to be configurable by a user. Typically, a hardware description language such as VHDL (Very High-Speed Integrated Circuit Hardware Description Language) is used in electronic design automation to describe digital and mixed-signal systems such as FPGA and ASIC. For example, an ASIC is manufactured based on VHDL programming provided pre-manufacturing, whereas logical components inside an FPGA may be configured based on VHDL programming, e.g., stored in a memory electrically connected to the FPGA circuit. In some examples, a combination of processor(s), ASIC(s), and/or FPGA circuits may be included in a computer.

A computer memory can be of any suitable type, e.g., EEPROM, EPROM, ROM, Flash, hard disk drives, solid state drives, servers, or any volatile or non-volatile media. The memory can store data, e.g., a memory of an ECU. The memory can be a separate device from the computer, and the computer can retrieve information stored in the memory, e.g., one or more computers 104 can obtain data to be stored via a vehicle network 112 in the vehicle 102, e.g., over an Ethernet bus, a CAN bus, a wireless network, etc. Alternatively, or additionally, the memory can be part of the computer, i.e., as a memory of the computer or firmware of a programmable chip.

The one or more vehicle computers 104 (e.g., one or more ECUs) can be included in a vehicle 102 that may be any suitable type of ground vehicle 102, e.g., a passenger or commercial automobile such as a sedan, a coupe, a truck, a sport utility, a crossover, a van, a minivan, etc. As part of autonomous driving system, a vehicle computer 104 may include programming to operate one or more of vehicle 102 brakes, propulsion (e.g., control of acceleration in the vehicle 102 by controlling one or more of an internal combustion engine, electric motor, hybrid engine, etc. and control power delivery therefrom), steering, climate control, interior and/or exterior lights, audio system, HMI, haptic/vibration mechanisms, etc., as well as to determine whether and when the computer, as opposed to a human operator, is to control such operations, such as by sending vehicle data over the vehicle network 112. Additionally, a vehicle computer 104 may be programmed to determine whether and when a human operator is to control such operations.

Vehicle computer 104 may include or be communicatively coupled to, e.g., via a vehicle network 112 such as a communications bus as described further below, more than one processor, e.g., included in sensors and cameras 108, electronic controller units (ECUs) or the like included in the vehicle 102 for monitoring and/or controlling various vehicle components, e.g., a powertrain controller, a brake controller, a steering controller, etc. The computer is generally arranged for communications on a vehicle 102 communication network that can include a bus in the vehicle 102 such as a controller area network (CAN) or the like, and/or other wired and/or wireless mechanisms. Alternatively, or additionally, in cases where the computer actually includes a plurality of devices, the vehicle network 112 may be used for communications between devices represented as the computer in this disclosure.

The vehicle network 112 is a network via which messages can be exchanged between various devices in vehicle 102. The vehicle computer 104 can be generally programmed to send and/or receive, via vehicle network 112, messages to and/or from other devices in vehicle 102 e.g., any or all of ECUs, sensors, cameras, actuators, components, communications module, a human machine interface HMI, etc. Additionally, or alternatively, messages can be exchanged among various such other devices in vehicle 102 via a vehicle network 112. In cases in which the vehicle computer 104 includes a plurality of devices, vehicle network 112 may be used for communications between devices represented as a computer in this disclosure. In some implementations, vehicle network 112 can be a network in which messages are conveyed via a vehicle 102 communications bus. For example, vehicle network 112 can include a controller area network (CAN) in which messages are conveyed via a CAN bus, or a local interconnect network (LIN) in which messages are conveyed via a LIN bus. In some implementations, vehicle network 112 can include a network in which messages are conveyed using other wired communication technologies and/or wireless communication technologies e.g., Ethernet, Wi-Fi, Bluetooth, Ultra-Wide Band (UWB), etc. Additional examples of protocols that may be used for communications over vehicle network 112 in some implementations include, without limitation, Media Oriented System Transport (MOST), Time-Triggered Protocol TTP, and FlexRay. In some implementations, vehicle network 112 can represent a combination of multiple networks, possibly of different types, that support communications among devices in vehicle 102. For example, vehicle network 112 can include a CAN in which some devices in vehicle 102 communicate via a CAN bus, and a wired or wireless local area network in which some device in vehicle 102 communicate according to Ethernet or WI-FI communication protocols.

The vehicle computer 104 and/or central computer 120 can communicate via a wide area network 116. Further, various computing devices discussed herein may communicate with each other directly, e.g., via direct radio frequency communications according to protocols such as Bluetooth or the like. For example, a vehicle 102 can include a communication module 110 to provide communications with devices and/or networks not included as part of the vehicle 102, such as the wide area network 116, for example. The communication module 110 can provide various communications, e.g., vehicle to vehicle (V2V), vehicle-to-infrastructure or everything (V2X) or vehicle-to-everything including cellular communications (C-V2X) wireless communications cellular, dedicated short range communications (DSRC), etc., to another vehicle or infrastructure typically via direct radio frequency communications and/or typically via the wide area network 116, e.g., to the central computer 120. The communication module 110 could include one or more mechanisms by which a vehicle computer 104 may communicate, including any desired combination of wireless e.g., cellular, wireless, satellite, microwave and radio frequency communication mechanisms and any desired network topology or topologies when a plurality of communication mechanisms are utilized. Exemplary communications provided via the module can include cellular, Bluetooth, IEEE 802.11, DSRC, cellular V2X, CV2X, and the like.

A vehicle 102 in accordance with the present disclosure includes a plurality of sensors and cameras 108 that may support the driving functions. For example, sensors and cameras 108 may include, but are not limited to, one or more wheel speed sensor, steering angle sensor, GPS sensor, user-facing camera, back-seat camera, forward-facing camera, side-facing camera, rear-facing camera, ultrasonic parking assist sensor, short range RADAR, medium range RADAR, LiDAR, light sensor, rain sensor, accelerometer, wheel torque sensors, inertial sensor, yaw rate sensor, etc. A vehicle 102 or other environment in accordance with the present disclosure also includes a plurality of sensors and cameras 108 that support the detection of sleeping and waking states, such as additional user-focused sensors including but not limited to an eye-tracking camera, an interior motion sensor, a touch sensor, a force sensor, a heart rate sensor, a respiration sensor, and/or a stress sensor that may be used to determine whether a user is asleep or awake.

A vehicle 102 or other environment in accordance with the present disclosure includes one or more stimulus mechanisms 105 that may be activated by computer 104 to attempt to awaken a user. A stimulus mechanism herein means a system or device that provides output detectable by a human user, e.g., that may be employed to awaken a user. Stimulus mechanisms 105 may include one or more sound transducers, such as the speakers of an audio system, one or more light sources, such as an overhead light or a dashboard mounted light or display, one or more haptic/vibration transducer, such as a seat-mounted vibration transducer or audio sub-woofer, and one or more climate control systems, such as an air conditioner/blower, heater/blower, and/or heated/cooled seat.

The stimulus mechanisms 105 may be connected to one or more vehicle computer 104 (e.g., ECU) via the vehicle network 112 and may receive signals to activate at various levels of intensity as part of a wake-up sequence.

A central computer 120 may be connected to a database 122. Data may be received by central computer 120 over wide area network 116 from communication module 110 of vehicle 102 and stored in database 122 to be accessed and used by central computer 120. Data from vehicle 102 may include calibrated wake-up sequences or other data related to effective wake-up mechanisms. In an implementation, the data may be used by a central computer 120 to aggregate data related to effective wake-up mechanisms from multiple users in order to determine or revise default wake-up mechanisms, such as by using an artificial intelligence (AI) or a machine learning (ML) algorithm.

Figure 2:
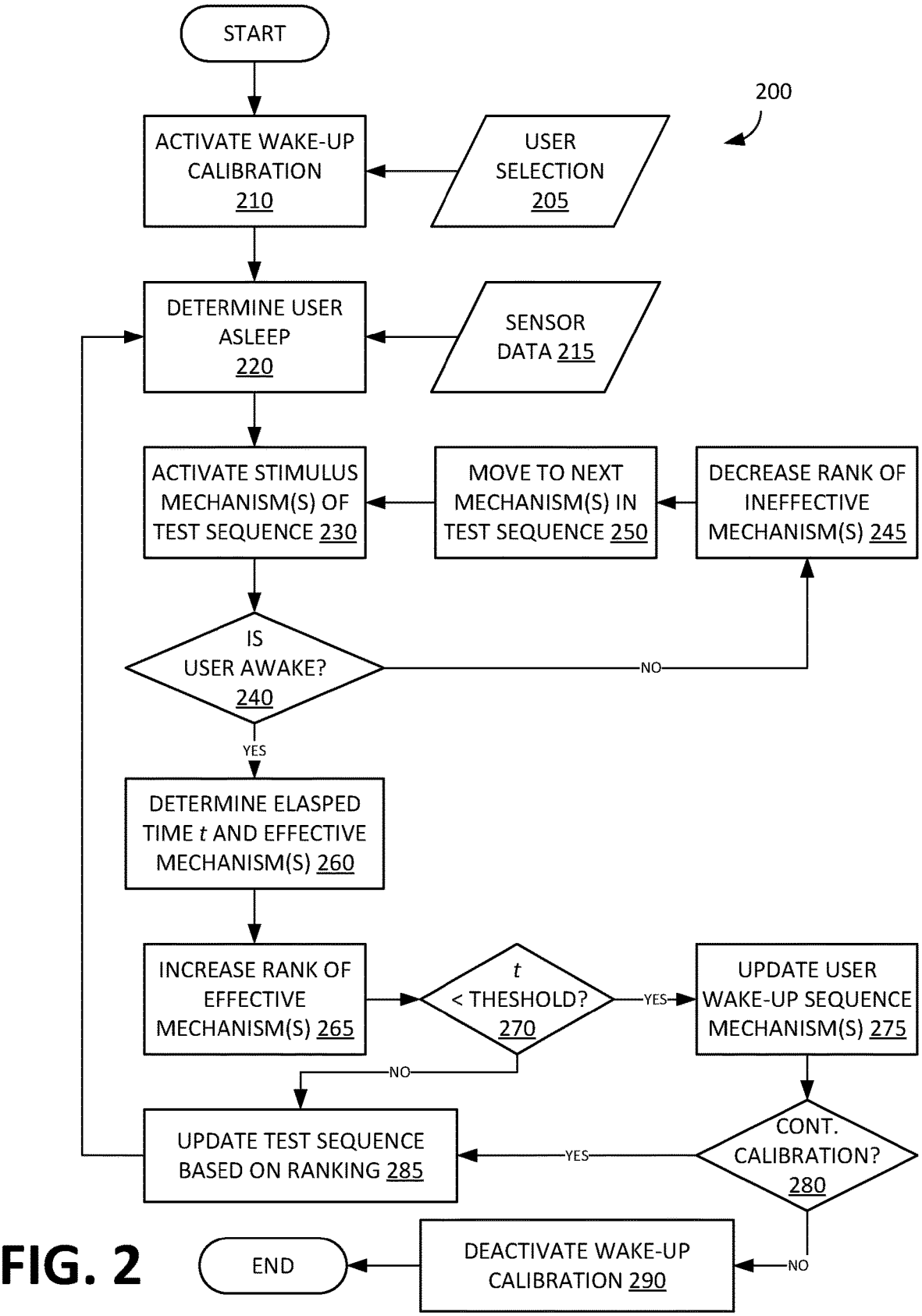
FIG. 2 is an example flow diagram for a process of calibrating a wake-up sequence.

With reference to FIG. 2, a process 200 may be used to determine a calibrated wake-up sequence for a user. Typically, the process 200 will be performed by one or more vehicle computers 104. While described with respect to an environment including a parked vehicle, this is but one example and other environments, e.g., security kiosks, are also possible with the scope of the present disclosure.

In a first block 210, the computer 104 may activate a wake-up sequence calibration for vehicle 102 based upon receiving input of a user selection 205 to perform the wake-up sequence calibration. For example, if computer 104 identifies a user in vehicle 102, such as by facial recognition based on camera data or by recognition of a user device such as a key-fob or mobile phone, the computer 104 may search for a calibrated wake-up sequence stored in a profile associated with the user. If the computer 104 determines that a calibrated wake-up sequence does not exist for the user, the computer 104 may display a prompt on a display of a human-machine interface (HMI) asking the user whether he/she would like to perform a wake-up sequence calibration, wherein a positive input at user selection 205 results in an activation of the wake-up sequence calibration for vehicle 102 for the user. In another implementation, a user may operate the HMI of the vehicle to a settings menu to provide input of the user selection 205.

In a next block 220, the computer 104 may determine that a user is asleep. This determination may be made based upon input of sensor data 215 by any suitable means, e.g., such as are known. For example, image recognition of camera data may determine that a user's eyes are closed for an extended period of time that is indicative of a sleep state, motion sensor data may determine that a user has not moved for an extended period of time that is indicative of a sleep state, a lack of data from a touch sensor or a force sensor over an extended period of time may be indicative of a sleep state, data from a heart rate sensor may indicate a slower heart rate associated with sleep, data from a respiration sensor may indicate slower respiration associated with sleep, and/or data from a stress sensor may indicate low levels of stress associated with a sleep state. The computer 104 may receive and identify various combinations of data from such sensors that are indicative of sleep to determine that the user is asleep at block 220.

Upon an occurrence of a condition in which the user should be awoken (i.e., a wake-up condition), the computer 104 may activate one or more stimulus mechanisms of a test wake-up sequence in a block 230 in order to attempt to wake the user. For example, the test wake-up sequence may comprise an ordered sequence that activates a first stimulus mechanism for a set period of time, activates a second stimulus mechanism for the set period of time, activates a third stimulus mechanism for the set period of time, activates a fourth stimulus mechanism for the set period of time, and then activates various combinations of the first to fourth stimulus mechanisms in tandem for the set period of time. In an implementation, an intensity of each of the stimulus mechanisms may increase (gradually or stepwise) from a low level to a high level during the set period or may be varied in a pattern, such as with pulses or with pulses of increasing intensity.

In order to gather data on the effectiveness of each of the various stimulus mechanisms and combinations thereof, the order of the stimulus mechanisms within a test wake-up sequence may be varied between successive activations of the test wake-up sequence. The order of the stimulus mechanisms within a test wake-up sequence may be varied randomly or may be varied in a particular sequence in order to obtain data on the least intrusive stimulus mechanisms in fewer iterations. For example, a light source stimulus mechanism and a haptic/vibration transducer stimulus mechanism may be considered less intrusive than a sound transducer stimulus mechanism or a climate control system stimulus mechanism, and thus these stimulus mechanisms may be placed earlier in the ordered sequences of the initial test wake-up sequences.

In another implementation, a user may indicate a preference for being woken with certain stimulus mechanisms, and the test wake-up sequences can include these stimulus mechanisms earlier in the ordered sequence, but may vary patterns and/or intensities of the activation of the preferred stimulus mechanisms to determine effective patterns and/or intensities.

In a next block 240, the computer 104 determines whether the user is awake (i.e., has awoken) during an activation of one or more of the stimulus mechanisms in the ordered sequence of the test wake-up sequence. This determination may be made based upon sensor data such as sensor data 215. For example, image recognition of camera data may determine that a user's eyes have opened and are indicative of a waking state, motion sensor data may determine that a user is moving in a manner indicative of a waking state, data from a touch sensor or a force sensor being operated may be indicative of a waking state, data from a heart rate sensor may indicate an increased heart rate associated with a waking state, data from a respiration sensor may indicate faster respiration associated with a waking state, and/or data from a stress sensor may indicate high levels of stress associated with a waking state. The computer 104 may determine that the user is awake upon detecting one or more various combinations of data from such sensors that have been specified to indicate that the user is awake.

If, at block 240, the user is not awake ("NO") upon the end of the set period for the activation of the one or more stimulus mechanisms in the ordered sequence of the test wake-up sequence, the test wake-up sequence can proceed to the next one or more stimulus mechanisms in the ordered sequence in a block 250, and proceed to activation of the next one or more stimulus mechanisms in the block 230.

Optionally, when the user is not awake ("NO") upon the end of the set period for the activation of the one or more stimulus mechanisms in the ordered sequence of the test wake-up sequence at block 240, the one or more stimulus mechanisms may be considered ineffective. In a block 245, the computer 104 may decrease a rank of the ineffective one or more stimulus mechanisms, wherein lower-ranked stimulus mechanisms may be placed later in the ordered sequence of subsequent test wake-up sequences so as to not waste time.

If, at block 240, the user is determined to be awake ("YES") during the set period for the activation of the one or more stimulus mechanisms in the ordered sequence of the test wake-up sequence, the one or more stimulus mechanisms is considered effective and the computer 104 determines an elapsed time t within the set period of activation at a block 260.

Optionally, when the one or more stimulus mechanisms in the ordered sequence of the test wake-up sequence is considered effective at block 260, the computer 104 may increase a rank of the effective one or more stimulus mechanisms in a block 265, wherein higher-ranked stimulus mechanisms may be placed earlier in the ordered sequence of subsequent test wake-up sequences so as to not waste time.

In a next block 270, the computer 104 may determine if the elapsed time t is less than a threshold time indicative of a sufficient wake-up time. This threshold time may be determined empirically or may be preset. In an implementation, the threshold time may be set by a user, and may vary based upon the particulars of the wake-up condition.

If, at block 270, the elapsed time t is less than the threshold time indicative of a sufficient wake-up time ("YES"), the process 200 moves to a block 275, wherein the computer 104 may update or calibrate the wake-up sequence for the user. In an implementation, a sequence of wake-up mechanisms for a user's wake-up sequence may be calibrated to use the one or more stimulus mechanisms having the lowest elapsed time t first, the next-lowest elapsed time 1 second, etc. A calibrated wake-up sequence may be saved in a profile associated with the user for later use.

In a next block 280, the computer 104 determines whether to continue the wake-up sequence calibration. For example, the computer 104 may have sufficient data to accurately rank the effectiveness of the various stimulus mechanisms for the user and determine a final calibrated wake-up sequence for the user. Similarly, the computer 104 may determine that one or more stimulus mechanisms has not been tested and determine that the collected data is insufficient. In another example, the computer 104 may prompt the user as to whether or not to continue the wake-up sequence calibration.

If either the computer 104 or the user determines not to continue the wake-up sequence calibration ("NO" at block 280), the computer 104 deactivates the wake-up sequence calibration at block 290 and the process 200 ends. Upon a next occurrence of a wake-up condition, the computer 104 may activate the one or more stimulus mechanisms as specified in the calibrated wake-up sequence stored for the user in order to wake the user.

If either the computer 104 or the user determines to continue the wake-up sequence calibration ("YES" at block 280), the process 200 moves to a block 285, wherein the computer 104 may update the test wake-up sequence based upon the ranking of the one or more stimulus mechanisms being effective and having an elapsed time t under the threshold time.

If, at block 270, the elapsed time t is not less than the threshold time indicative of a sufficient wake-up time ("NO"), the process 200 moves to a block 285, wherein the computer 104 may update the test wake-up sequence based upon the ranking of the one or more stimulus mechanisms being effective but over the threshold time.

Upon updating the test wake-up sequence in block 285, the process 200 continues to block 220, wherein the computer 104 determines whether the user is asleep, so as to perform another iteration in the wake-up sequence calibration.

While disclosed above with respect to certain implementations, various other implementations are possible without departing from the current disclosure.

Use of in response to, based on, and upon determining herein indicates a causal relationship, not merely a temporal relationship. Further, all terms used in the claims are intended to be given their plain and ordinary meanings as understood by those skilled in the art unless an explicit indication to the contrary is made herein. Use of the singular articles "a," "the," etc. should be read to recite one or more of the indicated elements unless a claim recites an explicit limitation to the contrary.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, unless indicated otherwise or clear from context, such processes could be practiced with the described steps performed in an order other than the order described herein. Likewise, it further should be understood that certain steps could be performed simultaneously, that other steps could be added, or that certain steps described herein could be omitted. In other words, the descriptions of processes herein are provided for the purpose of illustrating certain implementations and should in no way be construed so as to limit the present disclosure.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A system comprising a computer including a processor and a memory, the memory storing instructions executable by the processor programmed to:
   determine that a user is asleep based upon sensor data;
   activate one or more stimulus mechanisms for a set period of time in a test wake-up sequence upon occurrence of a wake-up condition;
   determine an elapsed time within the set period of time of the one or more stimulus mechanisms being activated in the test wake-up sequence at which the user wakes from sleep based on additional sensor data;
   compare the elapsed time to a threshold time indicative of a sufficient wake-up time; and
   determine a calibrated wake-up sequence including the one or more stimulus mechanisms having elapsed times below the threshold time.

2. The system of claim 1, further comprising instructions executable by the processor programmed to:
   initiate the system upon an activation by the user;
   prompt the user for continued use of the system upon determining the calibrated wake-up sequence; and
   terminate the system upon a deactivation by the user.

3. The system of claim 1, further comprising instructions executable by the processor programmed to:
   determine an identity of the user;
   order, within the calibrated wake-up sequence, the one or more stimulus mechanisms having elapsed times below the threshold time based upon lower elapsed times; and
   store the calibrated wake-up sequence for the user based upon the identity of the user.

4. The system of claim 1, wherein the one or more stimulus mechanisms include a light source, a sound transducer, a haptic/vibration transducer, and/or a climate control system.

5. The system of claim 1, wherein the test wake-up sequence comprises an ordered sequence of the one or more stimulus mechanisms including activation of a first stimulus mechanism, activation of a second stimulus mechanism, activation of a third stimulus mechanism, activation of a fourth stimulus mechanism, and activations of various combinations of the first, second, third, and fourth stimulus mechanisms; and
   wherein the activation of the first, second, third, and/or fourth stimulus mechanisms increases in intensity over an activation time.

6. The system of claim 1, wherein the sensor data and the additional sensor data is from a user-monitoring camera, a motion sensor, a heart-rate sensor, a respiration sensor, a stress sensor, a touch sensor, and/or a force sensor.

7. The system of claim 1, further comprising instructions executable by the processor programmed to vary the stimulus mechanisms or an order of the stimulus mechanisms in the test wake-up sequence to refine the calibrated wake-up sequence.

8. The system of claim 1, further comprising instructions executable by the processor programmed to transmit the calibrated wake-up sequence for the user to a remote server.

9. The system of claim 8, further comprising instructions executable by the processor programmed to receive a default wake-up sequence from the remote server based upon aggregated wake-up sequences of a plurality of users.

10. The system of claim 1, wherein the computer is a vehicle computer,
    wherein the sensor data and the additional sensor data is provided by sensors in a vehicle; and
    wherein the one or more stimulus mechanisms are disposed in the vehicle.

11. A method comprising:
determining that a user is asleep based upon sensor data;
activating one or more stimulus mechanisms for a set period of time in a test wake-up sequence upon occurrence of a wake-up condition;
determining an elapsed time within the set period of time of the one or more stimulus mechanisms being activated in the test wake-up sequence at which the user wakes from sleep based on additional sensor data;
comparing the elapsed time to a threshold time indicative of a sufficient wake-up time; and
determining a calibrated wake-up sequence including the one or more stimulus mechanisms having elapsed times below the threshold time.

12. The method of claim 11, further comprising:
initiating the method upon an activation by the user;
prompting the user for continued use of the method upon determining the calibrated wake-up sequence; and
terminating the method upon a deactivation by the user.

13. The method of claim 11, further comprising:
determining an identity of the user;
ordering, within the calibrated wake-up sequence, the one or more stimulus mechanisms having elapsed times below the threshold time based upon lower elapsed times; and
storing the calibrated wake-up sequence for the user based upon the identity of the user.

14. The method of claim 11, wherein the one or more stimulus mechanisms include a light source, a sound transducer, a haptic/vibration transducer, and/or a climate control system.

15. The method of claim 11, wherein the test wake-up sequence comprises an ordered sequence of the one or more stimulus mechanisms including activation of a first stimulus mechanism, activation of a second stimulus mechanism, activation of a third stimulus mechanism, activation of a fourth stimulus mechanism, and activations of various combinations of the first, second, third, and fourth stimulus mechanisms; and
wherein the activation of the first, second, third, and/or fourth stimulus mechanisms increases in intensity over an activation time.

16. The method of claim 11, wherein the sensor data and the additional sensor data is from a user-monitoring camera, a motion sensor, a heart-rate sensor, a respiration sensor, a stress sensor, a touch sensor, and/or a force sensor.

17. The method of claim 11, further comprising varying the stimulus mechanisms or an order of the stimulus mechanisms in the test wake-up sequence to refine the calibrated wake-up sequence.

18. The method of claim 11, further comprising transmitting the calibrated wake-up sequence for the user to a remote server.

19. The method of claim 18, further comprising receiving a default wake-up sequence from the remote server based upon aggregated wake-up sequences of a plurality of users.

20. The method of claim 11, wherein the user is in a vehicle,
wherein the sensor data and the additional sensor data is provided by sensors in the vehicle; and
wherein the one or more stimulus mechanisms are disposed in the vehicle.

* * * * *